United States Patent [19]

Keller

[11] Patent Number: 4,586,496

[45] Date of Patent: May 6, 1986

[54] SURGICAL CHISEL

[75] Inventor: Arnold Keller, Kayhude, Fed. Rep. of Germany

[73] Assignee: Waldemar Link GmbH & Co., Hamburg, Fed. Rep. of Germany

[21] Appl. No.: 707,782

[22] Filed: Mar. 4, 1985

[30] Foreign Application Priority Data

Mar. 5, 1984 [DE] Fed. Rep. of Germany ... 8406730[U]

[51] Int. Cl.⁴ .............................................. B25D 3/00
[52] U.S. Cl. .................................. 128/92 E; 128/305; 30/168; 30/167
[58] Field of Search ............... 128/304, 305, 310, 312, 128/92 EC, 92 E; D8/47; 30/168, 151, 164; 145/24, 26

[56] References Cited

U.S. PATENT DOCUMENTS

| | | | |
|---|---|---|---|
| 1,082,802 | 12/1913 | Full | 145/24 |
| 1,413,954 | 4/1922 | Ball et al. | 30/151 |
| 3,927,473 | 12/1975 | Braginetz | 30/164 |
| 4,497,355 | 2/1985 | Smith | 145/24 |

FOREIGN PATENT DOCUMENTS 596229  3/1978  U.S.S.R. ............................ 128/92 E

Primary Examiner—Robert P. Swiatek
Assistant Examiner—John G. Weiss
Attorney, Agent, or Firm—Townsend and Townsend

[57] ABSTRACT

A surgical chisel is formed by a flexurally rigid chisel shank and a thin, elongated chisel blade fixed at its front end, which are both displaceably guided in slideways in a chisel guide, which lends the chisel blade buckling resistance.

5 Claims, 13 Drawing Figures

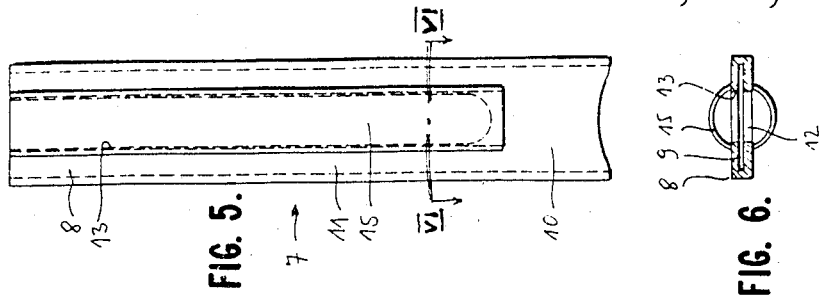
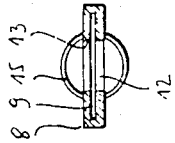
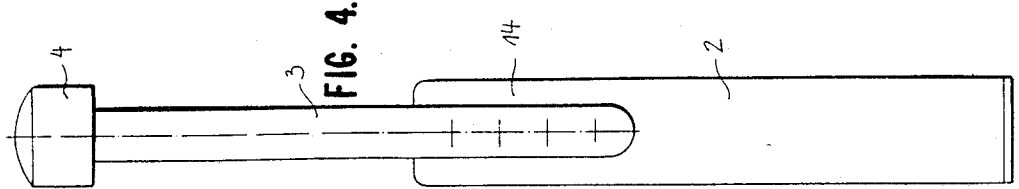
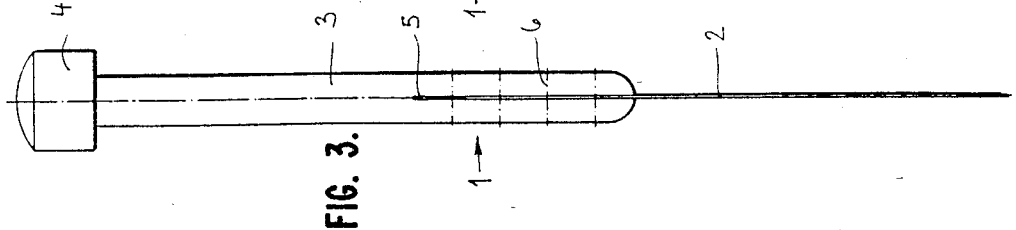
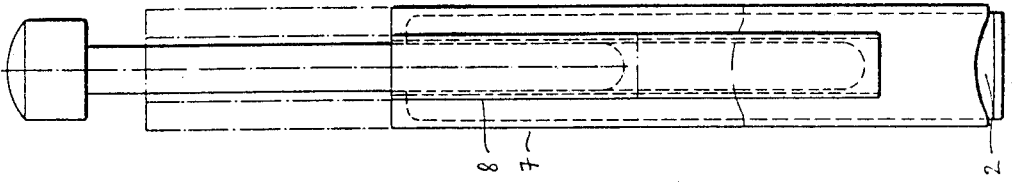
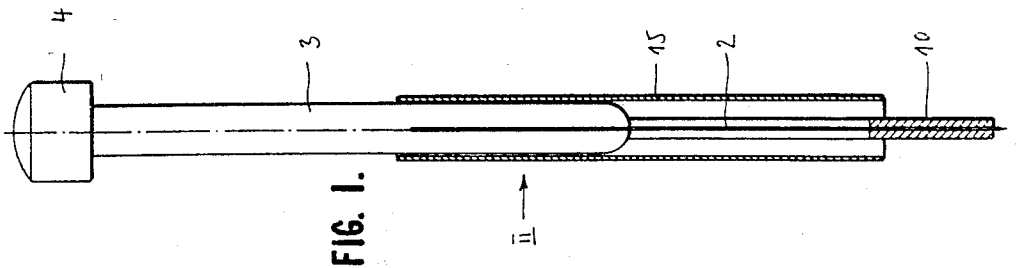

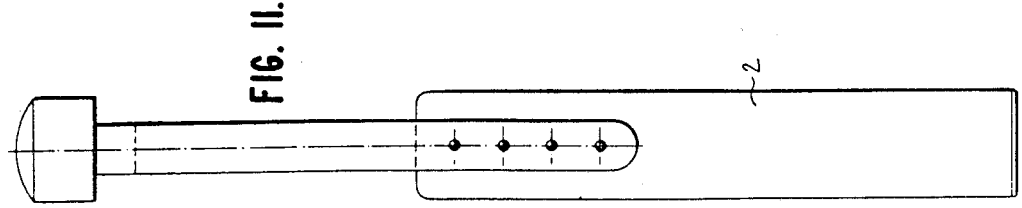
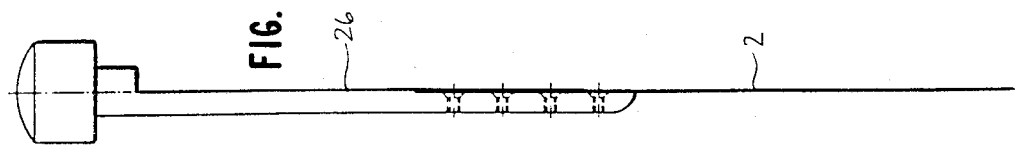
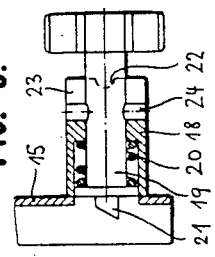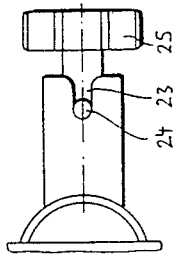
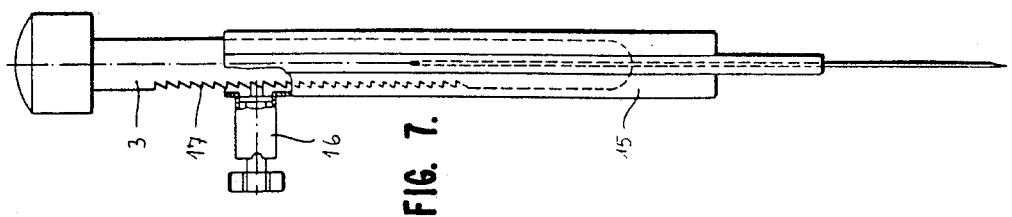

SURGICAL CHISEL

DESCRIPTION

Chisels are frequently used instruments in bone surgery and orthopedics for various cutting purposes, eg. for osteotomy or for the chiselling away of lamellae. They must have a considerable stability, in particular with respect to buckling load, which for a given chisel width is determined by the material thickness. The thickness must therefore be that much greater the greater the chisel length and the load to be expected. Whenever long stretches have to be severed, for example in osteotomies, chiselling in the upper head region of the femur, or chiselling away the articular surface of the tibia, not inconsiderable difficulties arise for the surgeon when using conventional chisels, due to the large chisel cross-section, namely in particular the risk of a premature and, in some cases, uncontrollable fracturing of the bone, excessive traumatism of the bone and the risk of jamming the chisel, which can then generally only be removed with difficulty.

The invention is based on the object of reducing these disadvantages.

The way in which this object is achieved according to the invention is that at the front end of a flexurally rigid chisel shank is fixed in the same direction an elongated, thin chisel blade, bearing at its front end the cutting edge, and that the chisel shank and the chisel blade are guided displaceably in their longitudinal direction in slideways of a flexurally rigid chisel guide.

Since, by virtue of the guide, the chisel blade can be very thin, eg. 0.5 or 1.0 or 1.5 or 2 mm, there is only a small widening of the cutting gap by the chisel thickness. The risk of premature fracturing and jamming is thereby decreased. The traumatism of the bone is reduced. However, the chisel has the necessary stability because, on the one hand, the chisel shank is securely guided in the chisel guide and therefore cannot deviate when struck and because, on the other hand, the chisel blade is protected in the chisel guide against buckling and is also guided in the object to be severed within the cutting gap in such a way that it cannot buckle. In this respect, the chisel guide is appropriately shaped in the manner of a sheath, from the front, narrow end of which the blade emerges. This shaping has the advantage that the chisel guide can be taken right up to the object to be severed, so that the chisel blade is not at any point exposed unguided to the risk of buckling. Although, due to its flexural rigidity, the thin blade according to the invention cannot guarantee a straight cut, as is the case with conventional chisels, a straight cut is nevertheless produced if the cutting edge is ground exactly to center and is thus made identical on the upper and lower flat sides. If required, the blade according to the invention also makes possible a cut along a curved path, namely by being ground asymmetrically.

The chisel according to the invention can also be used to particular advantage for very deep work, without the difficulties known in the use of conventional chisels having to be accepted. The width of the chisel blade can be of any size.

The chisel guide can have the same guide elements for the chisel blade and the chisel shank, namely opposing grooves in which the borders of the blade and corresponding projections of the chisel shank are displaceable. However, more appropriate are separate slideways for the chisel shank and the chisel blade.

It is advantageous if the chisel is lockable in the guide. This allows the required cutting depth to be set by correspondingly setting the length of the chisel blade projecting from the guide. This is useful, for example, when total severance is not wanted. It can be appropriate, furthermore, if the chisel is to be withdrawn from the bone against the chisel guide. This means that the blade is less exposed when withdrawing from the bone and reduces the risk of unwanted bending of the blade.

A chisel which is surrounded by a sleeve, the end plate of which is displaceable along the chisel against the force of a spring is known for making holes in walls for the purposes of electrical installations (DE-A No. 129 099). The end plate around the chisel and bearing under the spring force against the wall to be drilled is intended to prevent the crumbling of displaced plaster.

In order to hold a chisel driven forwards pneumatically at high frequency, it is known (WO-A No. 82/02 328) to attach on the chisel a sleeve which is vibration-insulated from the chisel. The chisel is, as such, flexurally rigid and is not guided by the sleeve with respect to buckling forces.

In the case of another known chisel (CH-A No. 405 193), the chisel is surrounded by a casing of tough, impact-resistant plastic, which laterally supports and insulates the steel core and which damps vibrations generated by the impact. The cross-section of the steel core can enlarge from the impact head and the working end towards the middle in the manner of a slender double cone whereby it is intended to increase the security against buckling rupture. If the cross-sectional dimensions of the steel core are compared with those of the plastic casing and the different moduluses of elasticity taken into account, the increase in buckling resistance due to the plastic casing can be negligible. This casing is not displaceable on the chisel.

In order to support a thin, steel wire-like punch, it is known (FR-A No. 964 389) to guide the punch in a sleeve consisting of several movable parts. In the section nearest the front, the sleeve has a diameter which is not substantially greater than the wire. Behind this, it forms a greater diameter for guiding displaceable guide parts receiving the wire in a corresponding bore, which guide parts are supported against each other by means of compression springs in order to have constantly a uniform distance from each other, even when advancing the wire, for optimum support of the wire.

In contrast, inherently flexurally rigid chisels have always been used as surgical chisels (FR-A No. 1 494 869) even when a slender cut is necessary.

The invention will be explained below in more detail, illustrated by advantageous exemplary embodiments and with reference to the drawing, in which:

FIG. 1 shows a side view of the instrument,

FIG. 2 shows a side view in viewing direction II of FIG. 1,

FIGS. 3 and 4 show a side view of the chisel in representations corresponding to FIGS. 1 and 2, FIG. 5 shows a side view, corresponding to FIG. 2, of the guide, FIG. 6 shows a sectional view along the line VI—VI of FIG. 5, FIG. 7 shows a side view, corresponding to FIG. 1, of an instrument with locking mechanism, FIGS. 8 and 9 show the locking mechanism in two mutually perpendicular views at an enlarged scale, FIGS. 10 and 11 show views of another embodiment of the chisel in representations corresponding to FIGS. 3 and 4, FIG. 12 shows a side view of the chisel guide associated with this embodiment, and FIG. 13 shows an end view of the chisel guide according to FIG. 12.

In the embodiment according to FIGS. 1 to 6, the chisel 1 consists of the chisel blade 2, which is formed by a metal sheet preferably of constant thickness and width, and the rear metal shank 3, which is formed by a cylindrical rod with impact head 4 and includes at its front end a center longitudinal slit 5 matching the thickness of the chisel blade 2 and in which the blade 2 is inserted centrally and fixed by means of screws 6, which are indicated by dot-dashed lines. When made of steel or steel-like material, the thickness of the chisel blade is preferably of the order of 0.2 to 2 mm and usually not substantially above 1.2 mm. the blade is made plane and is flush with the rear chisel part 3 from every side view. The chisel blade is wider than the chisel shank.

The chisel guide 7 encompasses a flat guide part 8, which includes a plane guide slit 9 for the chisel blade 2 to fit into. Whereas the flat guide part 8 is enclosed all round in its front section 10, in its rear part 11 it has a central recess 12 for receiving the rear chisel shank 3. The latter is guided by the edges 13 of the recess 12 and the borders 14 of the chisel blade projecting laterally beyond the shank and guided in the guide slit 9. If required, the flat guide part 8 can, moreover, be connected to a tube piece 15, which serves mainly as a protective tube and for holding the guide, but which can also form with its inner surface a guide surface for the rear chisel part, if required.

As seen in FIG. 3, the cutting edge of the blade is the same on both flat sides and is made symmetrical to center, so that a cut corresponding to the plane of the blade is produced.

FIG. 2 reveals the sheath in two relative positions with respect to the chisel, namely in a position represented by solid lines in which the chisel is withdrawn into the sheath, while in the position indicated by dot-dashed lines it is completely advanced.

The exemplary embodiment according to FIGS. 7 to 9 corresponds to that according to FIGS. 1 to 6 unless otherwise specified below. Arranged on the side of the pipe piece 15 of the sheath is a detent mechanism 16 which interacts with notches 17 of the rear chisel part 3.

As FIGS. 8 and 9 reveal, the detent mechanism consists of a socket 18 firmly connected to the pipe piece 15 and in which a bolt 19 is displaceably borne transverse to the chisel and is pushed towards the chisel by spring force 20. Its end 21 is shaped corresponding to the sawtooth-shaped notches of the chisel, the direction of the sawtooth shape being selected so that upon impact of the chisel the sheath must follow and upon withdrawal of the sheath the chisel must follow. The socket 18 forms at the extreme end two mutually perpendicular slits 22 and 23 of different lengths, which interact with a cross bolt 24 firmly connected to the bolt 19. In the position shown, the cross bolt 24 lies in the longer indentation 23, causing the bolt tip 21 to engage with the notching of the chisel. If the bolt 19 is withdrawn by means of the handle 25 and turned through 90°, so that the cross bolt engages with the recess 22, the bolt tip 21 is free from the notches of the chisel.

The embodiment of the chisel according to FIGS. 10 and 11 corresponds to that according to FIGS. 3 and 4 with the exception of the fact that the rear chisel part is cut away on one side 26 to be flush with the associated broad surface of the blade 2. Consequently, the sheath 7 only needs to have a recess 27 on one side (corresponding to the two-sided recess 12 of the embodiment described above). A protective tube 15 is not required in this case in general, although this design can of course also be provided with one.

I claim:

1. A surgical chisel, comprising:
   a chisel shank (3) having a first end adapted to receive the impact of a hammer;
   an elongated chisel blade (2) coupled at a first end to a second end of said chisel shank and having a cutting edge at a second end; and
   a chisel guide (7) having slideways for displaceably guiding said blade and shank in a longitudinal direction so that said guide supports and adds rigidity to said blade and shank.

2. The chisel of claim 1 wherein said guide has a sheathlike shape substantially surrounding said blade between said first and second ends, said slideways being shaped complementary to said blade.

3. The chisel of claim 1 wherein said slideways comprises first slideways shaped complementary to said blade and second slideways shaped complementary to said shank.

4. The chisel of claim 1 further comprising means for locking said guide to said chisel shank such that relative longitudinal movement is prevented.

5. A surgical chisel comprising:
   an elongated chisel shank (3) having a first end adapted to receive the impact of a hammer;
   an elongated chisel blade (2) coupled at a first end to a second end of said chisel shank and having a cutting edge at a second end;
   a chisel guide (7) having a first slideway completely surrounding a portion of said shank between said first and second ends of said shank and shaped complementary to said shank, and a second slideway completely surrounding a portion of said blade between said first and second ends of said blade and shaped complementary to said blade; and
   means for locking said guide to said chisel shank such that longitudinal movement of said shank relative to said guide is prevented.

* * * * *